(12) United States Patent
Coceancig

(10) Patent No.: US 9,113,958 B2
(45) Date of Patent: Aug. 25, 2015

(54) DISTRACTOR DEVICE AND A METHOD FOR DISTRACTING A JAW BONE

(76) Inventor: Paul Lloyd G. Coceancig, Newcastle (AU)

( * ) Notice: Subject to any disclaimer, the term of this patent is extended or adjusted under 35 U.S.C. 154(b) by 169 days.

(21) Appl. No.: 13/478,190

(22) Filed: May 23, 2012

(65) Prior Publication Data

US 2012/0303031 A1 Nov. 29, 2012

(30) Foreign Application Priority Data

May 23, 2011 (AU) ................................ 2011901990

(51) Int. Cl.
*A61B 17/60* (2006.01)
*A61B 17/66* (2006.01)
*A61B 17/80* (2006.01)

(52) U.S. Cl.
CPC ........... *A61B 17/663* (2013.01); *A61B 17/8071* (2013.01)

(58) Field of Classification Search
CPC ........................... A61B 17/663; A61B 17/8071
USPC ........... 606/57, 58, 105, 90, 280, 70, 71, 281, 606/282, 286; 433/173, 174
See application file for complete search history.

(56) References Cited

U.S. PATENT DOCUMENTS

| | | | |
|---|---|---|---|
| 5,885,283 A | 3/1999 | Gittleman | |
| 5,902,304 A | 5/1999 | Walker et al. | |
| 2005/0203628 A1 | 9/2005 | Elsalanty et al. | |
| 2005/0256526 A1 | 11/2005 | Johnston | |
| 2006/0079902 A1 | 4/2006 | Johnston | |
| 2009/0088766 A1 | 4/2009 | Magill et al. | |
| 2009/0192514 A1 | 7/2009 | Feinberg et al. | |
| 2010/0016900 A1 | 1/2010 | Terres et al. | |
| 2010/0152734 A1 | 6/2010 | Mulone | |

FOREIGN PATENT DOCUMENTS

| | | |
|---|---|---|
| WO | 03092519 A1 | 11/2003 |
| WO | 2006137045 A2 | 12/2006 |

OTHER PUBLICATIONS

International-type Search Report dated Aug. 31, 2011 corresponding to Australian Provisional Patent Application No. 2011901990, 3 pages.

KLS Martin; "The Zurich Pediatric Ramus Distractor".

(Continued)

*Primary Examiner* — Pedro Philogene
*Assistant Examiner* — David Comstock
(74) *Attorney, Agent, or Firm* — Maier & Maier, PLLC

(57) ABSTRACT

A distractor device for distracting a jaw bone divided by osteotomy into an anterior segment and a posterior segment. The distractor device comprises a body, an expansion member adapted to extend relative to the body, a first fixing member extending from the expansion member and having a first mounting portion adapted for mounting to one of the anterior and posterior segments, and a second fixing member extending from the body and having a second mounting portion adapted for mounting to the other of the anterior and posterior segments. In this embodiment, one of the first and second fixing members is shorter in length than the other fixing member, and a distance between the first and second mounting portions being adjustable by movement of the expansion member relative to the body to distract the jaw bone in use.

45 Claims, 8 Drawing Sheets

(56) References Cited

OTHER PUBLICATIONS

Pamela R. Hanson; "Treatment Planning and Orthodontic Management of Patients Undergoing Mandibular Distraction Osteogenesis"; Section V Indications and Treatment Planning; pp. 156-167.

Cornelius Klein; Extra Mandibular Distraction Osteogenesis Using the Frankfurt Modular Distraction System; Section IV Mandibular Lengthening and Wedding; pp. 187-195.

Patrick A. Diner et al; "Mandibular Lengthening Using Intraoral Distractors"; Section VI Mandibular Lengthening and Widening; pp. 247-255.

Makhail L. Samchukov et al.; "The Biomechanical Effects of Distraction Device Orientation During Mandibular Lengthening and Widening"; Section IV Biomechanical Considerations; pp. 131-146.

C. D'Hauthuille; "Comparison of Two Computer-Assisted Surgery Techniques to Guide a Mandibular Distraction Osteogenesis Procedure Technical Note"; International Journal of Oral & Maxillofacial Surgery; Surg. 2005; 34: pp. 197-201; available online at http://www.sciencedirect.com.

Radhika Chigurupati et al.; "Internal Mandibular Distraction to Relieve Airway Obstruction in Infants and Young Children With Micrognathia"; Pediatric Pulmonology (2004); pp. 230-235.

Aya Maeda et al; Orthodontic Treatment Combined With Mandibular Distraction Osteogenesis and Changes in Stomatognathic Function; Case Report; Angle Orthodontist, vol. 78, No. 6, 2008; pp. 1125-1132.

C. R. Mattick et al.; "Mandibular Advancement Using an Intra-Oral Osteogenic Distraction Technique; A Report of Three Clinical cases"; Clinical Section; Journal of Orthodontics; vol. 28; 2001; pp. 105-114.

Mandibular Retrognathia and Osteodistraction; Article for CPD Points; http://australasiandentist.realviewtechnologies.com/global/print.asp?path=/djvu/Gap . . . ; Nov. 29, 2012. 1 pg.

Harry C. Schwartz; "Reconstruction of the Ramus-Condyle Unit of the Temporomandibular Joint Using Transport Distraction"; Section 41; pp. 461-466.

F. Wolfgang Losken; "Planning of Mandibular Distraction"; Planning of Mandibular Distraction; Section 16; pp. 168-175.

DISTRACTOR DEVICE AND A METHOD FOR DISTRACTING A JAW BONE

RELATED APPLICATIONS

This application claims priority under 35 U.S.C. §119 to Australian Provisional Patent Application No. 2011901990 filed May 23, 2011, the disclosures of which are incorporated by reference herein in their entireties.

FIELD OF THE INVENTION

The present invention relates to distraction devices and in particular to a distractor device and a method for distracting a jaw bone.

The invention has been developed primarily for use in oral and maxillofacial surgery and will be described hereinafter with reference to this application. However, it will be appreciated that the invention is not limited to this particular field of use.

BACKGROUND OF THE INVENTION

Mandibular retrognathia in adolescents is an abnormal posterior positioning of the mandible relative to the facial skeleton and soft tissues. This abnormality leads to a number of secondary dental and facial developmental problems, most obviously a shortened lower jaw, which is unable to accommodate all the adult teeth resulting in severe crowding. In many circumstances, this abnormality can be corrected by jaw distraction, a method which involves first dividing a bone through osteotomy, i.e., cutting or fracturing a bone to create two segments separated by a gap or space, and then lengthening the bone member using devices known as distractors. Such distractor devices have fixing members, such as bone plates that are joined to each of the bone segments on opposite sides of the osteotomy, and a distraction or expansion member that allows the distance between the bone plates to be slowly increased over time, thereby allowing new bone growth to occur between the bone segments. The new bone growth increases in dimension until the proper bone length is achieved, at which time the distraction process is halted and the distractor device is removed. By placing an osteotomy cut between the first and second molars of the lower jaw, such jaw distraction surgery pre-emptively creates spaces by distracting the lower jaw forward, thus allowing for the creation of an orthodontic space for later orthodontic alignment of crowded lower dental arches.

When an osteotomy is made in the jaw bone using conventional distractor devices, and particularly the jaw bone of an adolescent, the space available between the closed bone plates of the distractor device located either side of the osteotomy is oftentimes too narrow to effectively fixate the bone plates without interfering with the actual osteotomy cut. As such, the bone plates must be located much further from the osteotomy than is necessary, which requires separation of the bone plates, and subsequently shortens the possible maximum displacement of the bone plates and thus the lengthening of the jaw bone that can be achieved through distraction. Also, because the osteotomy is made between the first and second molar teeth, bone plate fixation may impact upon, in particular the first molar tooth, compromising it, or, by virtue of attempting to fixate too long a forward bone plate before the osteotomy, displaces the line of the distraction vector below the occlusal plane of the lower jaw.

The present invention seeks to provide a distractor device and a method for distracting a jaw bone which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

According to a first aspect of the present invention, there is provided a distractor device for distracting a jaw bone divided by osteotomy into an anterior segment and a posterior segment, the distractor device comprising:

a body;

an expansion member adapted to extend relative to the body;

a first fixing member extending from the expansion member and having a first mounting portion adapted for mounting to one of the anterior and posterior segments; and a second fixing member extending from the body and having a second mounting portion adapted for mounting to the other of the anterior and posterior segments, one of the first and second fixing members being shorter in length than the other fixing member, a distance between the first and second mounting portions being adjustable by movement of the expansion member relative to the body to distract the jaw bone in use.

Advantageously, the first and second fixing members are of a different length such that the first and second mounting portions are substantially distanced from each other so as not to crowd the osteotomy, while the first and second fixing members are not otherwise separated by the expansion member, in order to accommodate the osteotomy cut.

Advantageously, the distance between the first and second mounting portions being adjustable by movement of the expansion member relative to the body enables the jaw bone to be distracted by virtue of the first and second mounting portions being mounted to a corresponding one of the anterior and posterior segments of the osteotomically separated jaw bone.

Advantageously, mounting of the first and second mounting portions to a corresponding one of the anterior and posterior segments of the osteotomically separated jaw bone is achievable via the patient's mouth.

Advantageously, mounting of the first and second mounting portions to a corresponding one of the anterior and posterior segments of the osteotomically separated jaw bone is not via making an incision in the patient's cheek and using a surgical trocar.

Advantageously, when mounted to a corresponding one of the anterior and posterior segments of the osteotomically separated jaw bone, the first and second mounting portions are sufficiently distanced from the first molar tooth so as not to damage the crown or roots of the tooth.

Preferably, the first mounting portion is mounted to the anterior segment and the second mounting portion is mounted to the posterior segment.

Advantageously, the first and second mounting portions being mounted to the anterior and posterior segments, respectively, ensures that as the expansion member is adjusted, the first mounting portion distracts the anterior segment from the posterior segment, thereby distracting the jaw bone.

Preferably, the first and second mounting portions each comprise at least three apertures arranged to define a triangle.

Advantageously, the triangular arrangement of apertures ensures that the first and second mounting portions are firmly mounted to a corresponding one of the anterior and posterior segments.

Preferably, the first mounting portion has a first aperture of the at least three apertures being located further from the body than the other apertures, and the second mounting portion has a first aperture of the at least three apertures being located closer to the body than the other apertures.

Advantageously, the triangular arrangements of apertures for the first and second mounting portions being oppositely oriented to each other, ensures that the distance between the first and second mounting portions is sufficient so as not to crowd the osteotomy.

Preferably, the first mounting portion has a first aperture of the at least three apertures being located closer to the body than the other apertures, and the second mounting portion has a first aperture of the at least three apertures being located further from the body than the other apertures.

Advantageously, the triangular arrangements of apertures for the first and second mounting portions being oppositely oriented to each other, ensures that the distance between the first and second mounting portions is sufficient so as not to crowd the osteotomy.

Preferably, the first and second mounting portions each have a first aperture of the at least three apertures being located further from the body than the other apertures.

Advantageously, as one of the first and second fixing members is shorter in length than the other fixing member, the triangular arrangement of apertures for the mounting portion of the shortest fixing member is distanced from the triangular arrangement of apertures for the mounting portion of the longer fixing member, such that the first and second mounting portions are substantially distanced from each other so as not to crowd the osteotomy, while the first and second fixing members are not otherwise separated by the expansion member, in order to accommodate the osteotomy cut.

Preferably, the first and second mounting portions each have a first aperture of the at least three apertures being located closer to the body than the other apertures.

Advantageously, as one of the first and second fixing members is shorter in length than the other fixing member, the triangular arrangement of apertures for the mounting portion of the shortest fixing member is distanced from the triangular arrangement of apertures for the mounting portion of the longer fixing member, such that the first and second mounting portions are substantially distanced from each other so as not to crowd the osteotomy, while the first and second fixing members are not otherwise separated by the expansion member, in order to accommodate the osteotomy cut.

Preferably, the first fixing member is shorter in length than the second fixing member.

Advantageously, the triangular arrangement of apertures for the first mounting portion is distanced from the triangular arrangement of apertures for the second mounting portion, such that the first and second mounting portions are substantially distanced from each other so as not to crowd the osteotomy, while the first and second fixing members are not otherwise separated by the expansion member, in order to accommodate the osteotomy cut.

Advantageously, the second fixing member being longer than the first fixing member enables it to be mounted onto an external oblique ridge of one of the anterior and posterior segments of the osteotomically separated jaw bone.

Advantageously, mounting of the second mounting portion of the second fixing member to a corresponding one of the anterior and posterior segments of the osteotomically separated jaw bone is achievable via the patient's mouth.

Advantageously, mounting of the second mounting portion of the second fixing member to a corresponding one of the anterior and posterior segments of the osteotomically separated jaw bone is not via making an incision in the patient's cheek and using a surgical trocar.

Advantageously, the first fixing member being shorter than the second fixing member ensures that it does not encroach towards the crown or root of the first molar tooth.

Preferably, the second fixing member is shorter in length than the first fixing member.

Advantageously, the triangular arrangement of apertures for the second mounting portion is distanced from the triangular arrangement of apertures for the first mounting portion of the, such that the first and second mounting portions are substantially distanced from each other so as not to crowd the osteotomy, while the first and second fixing members are not otherwise separated by the expansion member, in order to accommodate the osteotomy cut.

Preferably, the distractor device further comprises at least six fasteners, each fastener being adapted for locating in one of the at least three apertures of the first and second mounting portions to mount the first mounting portion to one of the anterior and posterior segments and the second mounting portion to the other of the anterior and posterior segments, respectively.

Advantageously, the first and second mounting portions are firmly mounted to a corresponding one of the anterior and posterior segments of the osteotomically separated jaw bone using fasteners.

Advantageously, the triangular arrangement of apertures ensures that when the fasteners are received in the apertures, the first and second mounting portions are firmly mounted to a corresponding one of the anterior and posterior segments.

Preferably, the expansion member comprises an externally threaded portion and the body comprises a complementary internally threaded portion to threadingly engage the externally threaded portion, the distance between the first and second mounting portions being adjustable by rotation of the expansion member relative to the body in use.

Advantageously, the distance between the first and second mounting portions is adjusted by rotation of the expansion member.

Preferably, the first fixing member is adapted to move linearly with respect to the second fixing member.

Advantageously, the first fixing member moving linearly with respect to the second fixing member ensures that the anterior segment of the jaw bone is distracted generally forwards of the posterior segment thereby distracting the jaw bone.

Preferably, each of the first and second fixing members is elongate and has a longitudinal axis.

Preferably, a centroid of the triangle of the at least three apertures of the first mounting portion is offset from the longitudinal axis of the first fixing member.

Advantageously, the centroid of the at least three apertures of the first mounting portion being offset ensures that the first and second mounting portions are substantially distanced from each other so as not to crowd the osteotomy.

Preferably, a centroid of the triangle of the at least three apertures of the second mounting portion is offset from the longitudinal axis of the second fixing member.

Advantageously, the centroid of the at least three apertures of the second mounting portion being offset ensures that the first and second mounting portions are substantially distanced from each other so as not to crowd the osteotomy.

According to a second aspect of the present invention, there is provided a distractor device for distracting a jaw bone divided by osteotomy into an anterior segment and a posterior segment, the distractor device comprising:
- a body;
- an expansion member adapted to extend relative to the body;
- a first fixing member extending from the expansion member and having a first mounting portion adapted for mounting to one of the anterior and posterior segments; and
- a second fixing member extending from the body and having a second mounting portion adapted for mounting to other of the anterior and posterior segments, the first and second mounting portions each comprising at least three apertures arranged to define a triangle, one of the first and second mounting portions having a first aperture of the at least three apertures being located further from the body than the other apertures, and the other of the first and second mounting portions having a first aperture of the at least three apertures being located closer to the body than the other apertures, a distance between the first and second mounting portions being adjustable by movement of the expansion member relative to the body to distract the jaw bone in use.

Advantageously, mounting of the first and second mounting portions to a corresponding one of the anterior and posterior segments of the osteotomically separated jaw bone is achievable via the patient's mouth.

Advantageously, mounting of the first and second mounting portions to a corresponding one of the anterior and posterior segments of the osteotomically separated jaw bone is not via making an incision in the patient's cheek and using a surgical trocar.

Advantageously, when mounted to a corresponding one of the anterior and posterior segments of the osteotomically separated jaw bone, the first and second mounting portions are sufficiently distanced from the first molar tooth so as not to damage the crown or roots of the tooth.

Advantageously, the distance between the first and second mounting portions being adjustable by movement of the expansion member relative to the body enables the jaw bone to be distracted by virtue of the first and second mounting portions being mounted to a corresponding one of the anterior and posterior segments of the osteotomically separated jaw bone.

Advantageously, the triangular arrangement of apertures ensures that the first and second mounting portions are firmly mounted to a corresponding one of the anterior and posterior segments.

Advantageously, the triangular arrangements of apertures for the first and second mounting portions being oppositely oriented to each other, ensures that the distance between the first and second mounting portions is sufficient so as not to crowd the osteotomy.

Preferably, the first mounting portion is mounted to the anterior segment and the second mounting portion is mounted to the posterior segment.

Advantageously, the first and second mounting portions being mounted to the anterior and posterior segments, respectively, ensures that as the expansion member is adjusted, the distractor device distracts the anterior segment from the posterior segment, thereby distracting the jaw bone.

Preferably, the first mounting portion has the first aperture of the at least three apertures being located further from the body than the other apertures.

Advantageously, the triangular arrangements of apertures for the first and second mounting portions being oppositely oriented to each other, ensures that the distance between the first and second mounting portions is sufficient so as not to crowd the osteotomy.

Preferably, the first mounting portion has the first aperture of the at least three apertures being located closer to the body than the other apertures.

Advantageously, the triangular arrangements of apertures for the first and second mounting portions being oppositely oriented to each other, ensures that the distance between the first and second mounting portions is sufficient so as not to crowd the osteotomy.

Preferably, the first fixing member is shorter in length than the second fixing member.

Advantageously, the triangular arrangement of apertures for the first mounting portion is distanced from the triangular arrangement of apertures for the second mounting portion of the, such that the first and second mounting portions are substantially distanced from each other so as not to crowd the osteotomy, while the first and second fixing members are not otherwise separated by the expansion member, in order to accommodate the osteotomy cut.

Advantageously, the second fixing member being longer than the first fixing member enables it to be mounted onto an external oblique ridge of one of the anterior and posterior segments of the osteotomically separated jaw bone.

Advantageously, the first fixing member being shorter than the second fixing member ensures that it does not encroach towards the crown or root of the first molar tooth.

Preferably, the second fixing member is shorter in length than the first fixing member.

Advantageously, the triangular arrangement of apertures for the second mounting portion is distanced from the triangular arrangement of apertures for the first mounting portion of the, such that the first and second mounting portions are substantially distanced from each other so as not to crowd the osteotomy, while the first and second fixing members are not otherwise separated by the expansion member, in order to accommodate the osteotomy cut.

Preferably, the distractor device further comprises at least six fasteners, each fastener being adapted for locating in one of the at least three apertures of the first and second mounting portions to mount the first mounting portion to one of the anterior and posterior segments and the second mounting portion to the other of the anterior and posterior segments, respectively.

Advantageously, the first and second mounting portions are firmly mounted to the anterior and posterior segments, respectively, of the osteotomically separated jaw bone using fasteners.

Advantageously, the triangular arrangement of apertures ensures that when the fasteners are received in the apertures, the first and second mounting portions are firmly mounted to the anterior and posterior segments, respectively.

Preferably, the expansion member comprises an externally threaded portion and the body comprises a complementary internally threaded portion to threadingly engage the externally threaded portion, the distance between the first and second mounting portions being adjustable by rotation of the expansion member relative to the body in use.

Advantageously, the distance between the first and second mounting portions is adjusted by rotation of the expansion member.

Preferably, the first fixing member is adapted to move linearly with respect to the second fixing member.

Advantageously, the first fixing member moving linearly with respect to the second fixing member ensures that the anterior segment of the jaw bone is distracted generally forwards of the posterior segment thereby distracting the jaw bone.

Preferably, each of the first and second fixing members is elongate and has a longitudinal axis.

Preferably, a centroid of the triangle of the at least three apertures of the first mounting portion is offset from the longitudinal axis of the first fixing member.

Advantageously, the centroid of the at least three apertures of the first mounting portion being offset ensures that the first and second mounting portions are substantially distanced from each other so as not to crowd the osteotomy.

Preferably, a centroid of the triangle of the at least three apertures of the second mounting portion is offset from the longitudinal axis of the second fixing member.

Advantageously, the centroid of the at least three apertures of the second mounting portion being offset ensures that the first and second mounting portions are substantially distanced from each other so as not to crowd the osteotomy.

According to a third aspect of the present invention, there is provided a distractor device for distracting a jaw bone divided by osteotomy into an anterior segment and a posterior segment, the distractor device comprising:
  a body;
  an expansion member adapted to extend relative to the body along a vector of distraction;
  a first fixing member extending from the expansion member and having a first mounting portion having a first mounting surface, the first mounting surface being adapted for mounting to one of the anterior and posterior segments; and
  a second fixing member extending from the body and having a second mounting portion having a second mounting surface, the second mounting surface being adapted for mounting to the other of the anterior and posterior segments, the first mounting surface and the second mounting surface being in a substantially same plane and oriented at an angle of between 0.1 degrees and 30 degrees to the vector of distraction, a distance between the first and second mounting portions being adjustable by movement of the expansion member relative to the body to distract the jaw bone in use.

Advantageously, mounting of the first and second mounting portions to a corresponding one of the anterior and posterior segments of the osteotomically separated jaw bone is achievable via the patient's mouth.

Advantageously, mounting of the first and second mounting portions to a corresponding one of the anterior and posterior segments of the osteotomically separated jaw bone is not via making an incision in the patient's cheek and using a surgical trocar.

Advantageously, when mounted to a corresponding one of the anterior and posterior segments of the osteotomically separated jaw bone, the first and second mounting portions are sufficiently distanced from the first molar tooth so as not to damage the crown or roots of the tooth.

Advantageously, the mounting surfaces of the first and second mounting portions being angled relative to the vector of distraction reduces flaring of the posterior segment during distraction.

Advantageously, the mounting surfaces of the first and second mounting portions being angled relative to the vector of distraction enables flaring of the posterior segment to be modified in relation to distraction.

Advantageously, reducing flaring of the posterior segment increases the chances of the upper and lower molars interdigitating.

Advantageously, the mounting surfaces of the first and second mounting portions being angled relative to the vector of distraction reduces the risk of a cross bite occurring between the respective second molars of the upper and lower jaw, and a subsequent anterior open bite developing between the front or forward incisor teeth of each jaw as distraction proceeds.

Advantageously, the distance between the first and second mounting portions being adjustable by movement of the expansion member relative to the body enables the jaw bone to be distracted by virtue of the first and second mounting portions being mounted to a corresponding one of the anterior and posterior segments of the osteotomically separated jaw bone.

Preferably, the first mounting surface is mounted to the anterior segment and the second mounting surface is mounted to the posterior segment.

Advantageously, the first and second mounting surfaces being mounted to the anterior and posterior segments, respectively, ensures that as the expansion member is adjusted, the distractor device distracts the anterior segment from the posterior segment, thereby distracting the jaw bone.

Preferably, the angle is between 5 degrees and 15 degrees.

Advantageously, the mounting surfaces of the first and second mounting portions being angled relative to the longitudinal axis of the body enables flaring of the posterior segment to be modified in relation to distraction.

Preferably, the vector of distraction is aligned with the longitudinal axis of the body.

Advantageously, the anterior segment is distracted along the distraction vector aligned with the longitudinal axis of the body.

Preferably, one of the first and second fixing members is shorter in length than the other fixing member.

Advantageously, one of the first and second fixing members being shorter in length than the other fixing member ensures that the corresponding first and second mounting portions are substantially distanced from each other so as not to crowd the osteotomy, while the first and second fixing members are not otherwise separated by the expansion member, in order to accommodate the osteotomy cut.

Preferably, the first fixing member is shorter in length than the second fixing member.

Advantageously, the first fixing member being shorter in length than the second fixing member ensures that the corresponding first and second mounting portions are substantially distanced from each other so as not to crowd the osteotomy, while the first and second fixing members are not otherwise separated by the expansion member, in order to accommodate the osteotomy cut.

Advantageously, the second fixing member being longer than the first fixing member enables it to be mounted onto an external oblique ridge of one of the anterior and posterior segments of the osteotomically separated jaw bone.

Advantageously, the first fixing member being shorter than the second fixing member ensures that it does not encroach towards the crown or root of the first molar tooth.

Preferably, the second fixing member is shorter in length than the first fixing member.

Advantageously, the second fixing member being shorter in length than the first fixing member ensures that the corresponding second and first mounting portions are substantially distanced from each other so as not to crowd the osteotomy, while the first and second fixing members are not otherwise separated by the expansion member, in order to accommodate the osteotomy cut.

Preferably, the first and second mounting portions each comprise at least three apertures arranged to define a triangle.

Advantageously, the triangular arrangement of apertures ensures that the first and second mounting surfaces are firmly mounted to a corresponding one of the anterior and posterior segments.

Preferably, the first mounting portion has a first aperture of the at least three apertures being located further from the body than the other apertures, and the second mounting portion has a first aperture of the at least three apertures being located closer to the body than the other apertures.

Advantageously, the triangular arrangements of apertures for the first and second mounting portions being oppositely oriented to each other, ensures that the distance between the first and second mounting portions is sufficient so as not to crowd the osteotomy.

Preferably, the first mounting portion has a first aperture of the at least three apertures being located closer to the body than the other apertures, and the second mounting portion has a first aperture of the at least three apertures being located further from the body than the other apertures.

Advantageously, the triangular arrangements of apertures for the first and second mounting portions being oppositely oriented to each other, ensures that the distance between the first and second mounting portions is sufficient so as not to crowd the osteotomy.

Preferably, the first and second mounting portions each have a first aperture of the at least three apertures being located further from the body than the other apertures.

Preferably, the first and second mounting portions each have a first aperture of the at least three apertures being located closer to the body than the other apertures.

Preferably, the distractor device further comprises at least six fasteners, each fastener being adapted for locating in one of the at least three apertures of the first and second mounting portions to mount the first mounting surface to one of the anterior and posterior segments and the second mounting surface to the other of the anterior and posterior segments, respectively.

Advantageously, the first and second mounting surfaces are firmly mounted to a corresponding one of the anterior and posterior segments of the osteotomically separated jaw bone using fasteners.

Advantageously, the triangular arrangement of apertures ensures that when the fasteners are received in the apertures, the first and second mounting surfaces are firmly mounted to a corresponding one of the anterior and posterior segments.

Preferably, the expansion member comprises an externally threaded portion and the body comprises a complementary internally threaded portion to threadingly engage the externally threaded portion, the distance between the first and second mounting portions being adjustable by rotation of the expansion member relative to the body in use.

Advantageously, the distance between the first and second mounting portions is adjusted by rotation of the expansion member.

Preferably, the first fixing member is adapted to move linearly with respect to the second fixing member.

Advantageously, the first fixing member moving linearly with respect to the second fixing member ensures that the anterior segment of the jaw bone is distracted generally forwards of the posterior segment thereby extending the jaw bone.

Preferably, each of the first and second fixing members is elongate and has a longitudinal axis.

Preferably, a centroid of the triangle of the at least three apertures of the first mounting portion is offset from the longitudinal axis of the first fixing member.

Advantageously, the centroid of the at least three apertures of the first mounting portion being offset ensures that the first and second mounting portions are substantially distanced from each other so as not to crowd the osteotomy.

Preferably, a centroid of the triangle of the at least three apertures of the second mounting portion is offset from the longitudinal axis of the second fixing member.

Advantageously, the centroid of the at least three apertures of the second mounting portion being offset ensures that the first and second mounting portions are substantially distanced from each other so as not to crowd the osteotomy.

According to a fourth aspect of the present invention, there is provided a method of distracting a jaw bone of a person divided by osteotomy into an anterior segment and at least one posterior segment using at least one distractor device, the method comprising the steps of:

attaching a first mounting portion of the at least one distractor device to one of the anterior segment and the at least one posterior segment;

attaching a second mounting portion of the at least one distractor device to the other segment of the anterior segment and the at least one posterior segment, such that the first and second mounting portions are attached across the osteotomy; and distracting the anterior segment from the at least one posterior segment in an anterior direction along a distraction vector that slopes upwardly towards an occlusal plane of the lower jaw of the person.

Advantageously, the anterior segment is forwardly and upwardly distracted relative to the occlusal plane of the lower jaw.

Advantageously, the anterior segment is not distracted along a direction vector that has a downward component relative to the occlusal plane of the lower jaw.

Preferably, the angle subtended by the distraction vector and the occlusal plane of the lower jaw is between 0.1 and 25 degrees.

Preferably, the angle subtended by the distraction vector and the occlusal plane of the lower jaw is between 0.2 and 20 degrees.

Preferably, the at least one distractor device is two distractor devices, the first and second mounting portions of a first of the two distractor devices being attached to a left mandible and the first and second mounting portions of a second of the two distractor devices being attached to a right mandible.

Advantageously, when the left and right mandibles of the jaw bone are divided by osteotomy cuts, the resulting anterior segment is bilaterally distracted from the posterior segment of each mandible.

Preferably, the at least one posterior segment is two posterior segments, the first mounting portion of each of the two distractor devices being attached to the anterior segment and the second mounting portion of each of the two distractor devices being attached across the osteotomy to a corresponding posterior segment of the two posterior segments.

Advantageously, the first and second mounting portions of each distractor device being mounted to the anterior and posterior segments, respectively, ensures that as the expansion members are adjusted, the distractor devices bilaterally distract the anterior segment from the posterior segments, thereby distracting the jaw bone.

Preferably, the anterior segment is distracted from the at least one posterior segment by between 0.2 mm and 2.0 mm each day.

Advantageously, the distraction distance can be varied between 0.2 mm and 2.0 mm each day until the desired amount of distraction is achieved.

Preferably, the anterior segment is distracted from the at least one posterior segment by between 0.5 mm and 1.5 mm each day.

Advantageously, the distraction distance can be varied between 0.5 mm and 1.5 mm each day until the desired amount of distraction is achieved.

Preferably, the anterior segment is distracted from the at least one posterior segment by between 0.7 mm and 1.2 mm each day.

Advantageously, the distraction distance can be varied between 0.7 mm and 1.2 mm each day until the desired amount of distraction is achieved.

Preferably, the method further comprises the step of:
repeating the distracting step until the desired amount of distraction is achieved.

Advantageously, distraction is repeated until the desired distraction distance is achieved.

According to a fifth aspect of the present invention, there is provided a method of distracting a jaw bone of a person divided by osteotomy into an anterior segment and at least one posterior segment using at least one distractor device, the method comprising the steps of:
attaching a first mounting portion of the at least one distractor device to one of the anterior segment and the at least one posterior segment;
attaching a second mounting portion of the at least one distractor device to the other segment of the anterior segment and the at least one posterior segment, such that the first and second mounting portions are attached across the osteotomy; and
distracting the anterior segment from the at least one posterior segment in an anterior direction along a distraction vector that is substantially parallel to an occlusal plane of the lower jaw of the person.

Advantageously, the anterior segment is forwardly distracted along a direction vector that is substantially parallel to the occlusal plane of the lower jaw.

Advantageously, the anterior segment is not distracted along a direction vector that has a downward component relative to the occlusal plane of the lower jaw.

Preferably, the at least one distractor device is two distractor devices, the first and second mounting portions of a first of the two distractor devices being attached to a left mandible and the first and second mounting portions of a second of the two distractor devices being attached to a right mandible.

Advantageously, when the left and right mandibles of the jaw bone are divided by osteotomy cuts, the resulting anterior segment is bilaterally distracted from the posterior segment of each mandible.

Preferably, the at least one posterior segment is two posterior segments, the first mounting portion of each of the two distractor devices being attached to the anterior segment and the second mounting portion of each of the two distractor devices being attached across the osteotomy to a corresponding posterior segment of the two posterior segments.

Advantageously, the first and second mounting portions of each distractor device being mounted to the anterior and posterior segments, respectively, ensures that as the expansion members are adjusted, the distractor devices bilaterally distract the anterior segment from the posterior segments, thereby distracting the jaw bone.

Preferably, the anterior segment is distracted from the at least one posterior segment by between 0.2 mm and 2.0 mm each day.

Advantageously, the distraction distance can be varied between 0.2 mm and 2.0 mm each day until the desired amount of distraction is achieved.

Preferably, the anterior segment is distracted from the at least one posterior segment by between 0.5 mm and 1.5 mm each day.

Advantageously, the distraction distance can be varied between 0.5 mm and 1.5 mm each day until the desired amount of distraction is achieved.

Preferably, the anterior segment is distracted from the at least one posterior segment by between 0.7 mm and 1.2 mm each day.

Advantageously, the distraction distance can be varied between 0.7 mm and 1.2 mm each day until the desired amount of distraction is achieved.

Preferably, the method further comprises the step of:
repeating the distracting step until the desired amount of distraction is achieved.

Advantageously, distraction is repeated until the desired distraction distance is achieved.

Other aspects of the invention are also disclosed.

BRIEF DESCRIPTION OF THE DRAWINGS

Notwithstanding any other forms which may fall within the scope of the present invention, preferred embodiments of the invention will now be described, by way of example only, with reference to the accompanying drawings in which.

DETAILED DESCRIPTION OF SPECIFIC EMBODIMENTS

Figure 1:
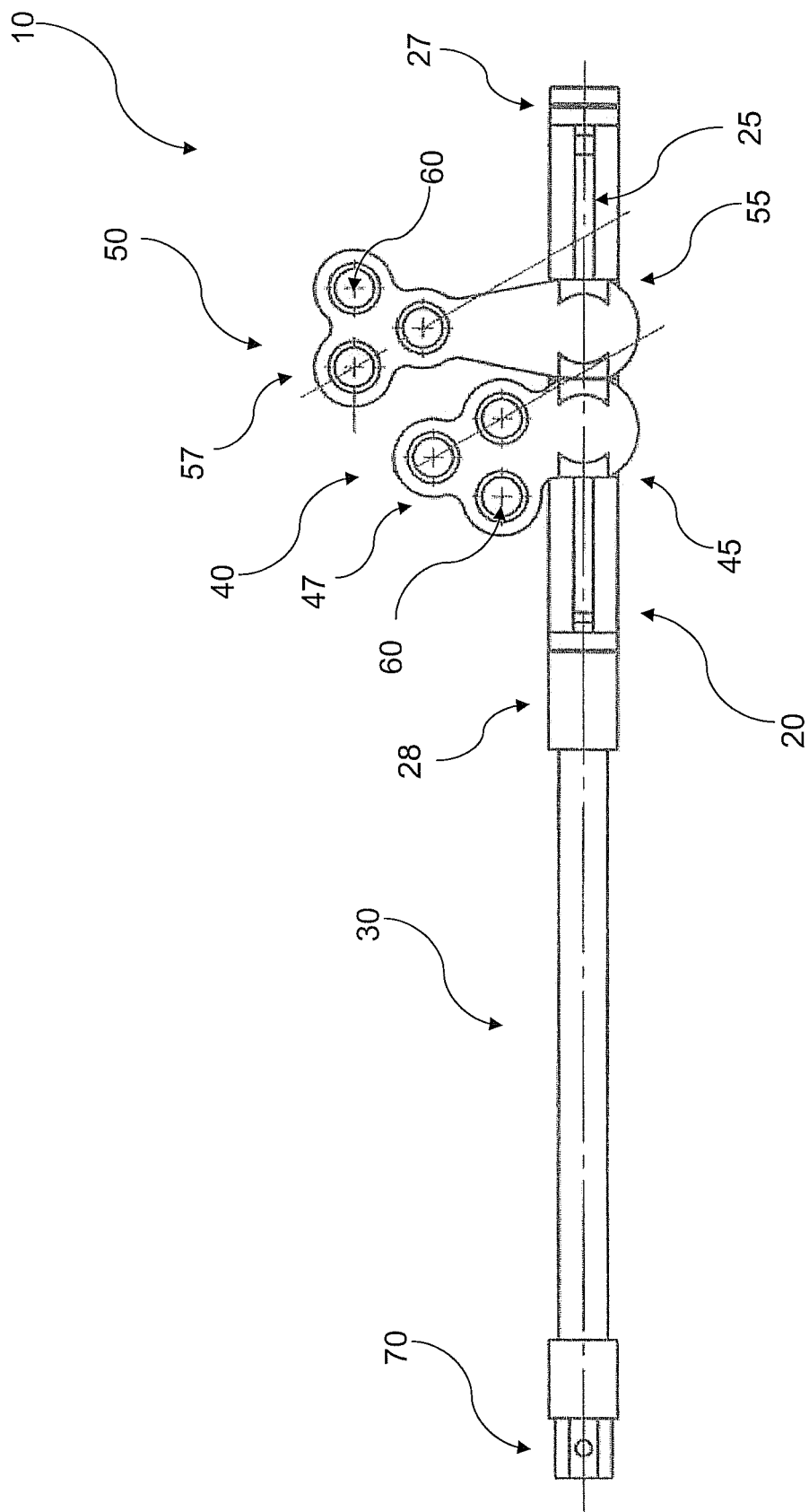
FIG. 1 is a side view of a distractor device in accordance with a preferred embodiment of the present invention, the distractor device comprising a first fixing member having a first mounting portion and a second fixing member having a second mounting portion.

It should be noted in the following description that like or the same reference numerals in different embodiments denote the same or similar features.

As shown in FIG. 1, a distractor device 10 is provided for distracting a jaw bone (not shown) of a patient that has been divided by osteotomy into an anterior segment (not shown) and a posterior segment (not shown) according to a preferred embodiment of the present invention. The distractor device 10 comprises a body 20 that is elongate and has a generally hollow cylindrical shape that is capped at a first end with end cap 27. The body 20 comprises a longitudinal groove 25 that extends partly along the length of the body 20 and is stoppered at the first end by the first end cap 27 and stoppered at the other end by a hollow sleeve 28. The groove 25 extends through the outer wall of the hollow cylindrical body 20. The body 20 is manufactured from surgical stainless steel. Although, it will be appreciated that in other embodiments, the body 20 may be manufactured from any suitable biomedical material appropriate for surgical use, including, but not limited to: titanium.

As shown in FIG. 1, the distractor device 10 further comprises a flexible elongate activator 30 comprising an externally threaded portion (not shown) extending generally along the length of the activator 30. The body 20 comprises a complementary internally threaded portion (not shown) to threadingly receive a first end of the externally threaded portion of the activator 30 therein. A second end of the activator 30, which extends out from the hollow sleeve 28 of the body 20, comprises a turnkey 70 to enable a user to manually rotate the activator 30 any required number of turns to adjust the length of the activator 30 relative to the body 20.

In other embodiments, the activator is 30 not limited to being flexible and may therefore be rigid depending on the intraoral application of the distractor device 10.

The distractor device 10 further comprises a first fixing member 40 having an end portion 45 that is located within the longitudinal groove 25 of the body 20 and mounted to the activator 30. The first fixing member 40 comprises a first mounting portion 47 located distal to the end portion 45 of the first fixing member 40. The first mounting portion 47 has a first mounting surface that is adapted for mounting to the anterior segment of the jaw bone.

The distractor device 10 further comprises a second fixing member 50 having an end portion 55 that is fixed within the longitudinal groove 25 of the body 20. The second fixing member 50 has a longitudinal axis that is oriented at a generally 90 degree angle to the longitudinal axis of the body 20. The second fixing member 50 comprises a second mounting portion 57 located distal to the end portion 55 of the second fixing member 50. The second mounting portion 57 has a second mounting surface adapted for mounting to the posterior segment of the jaw bone.

Figure 5:
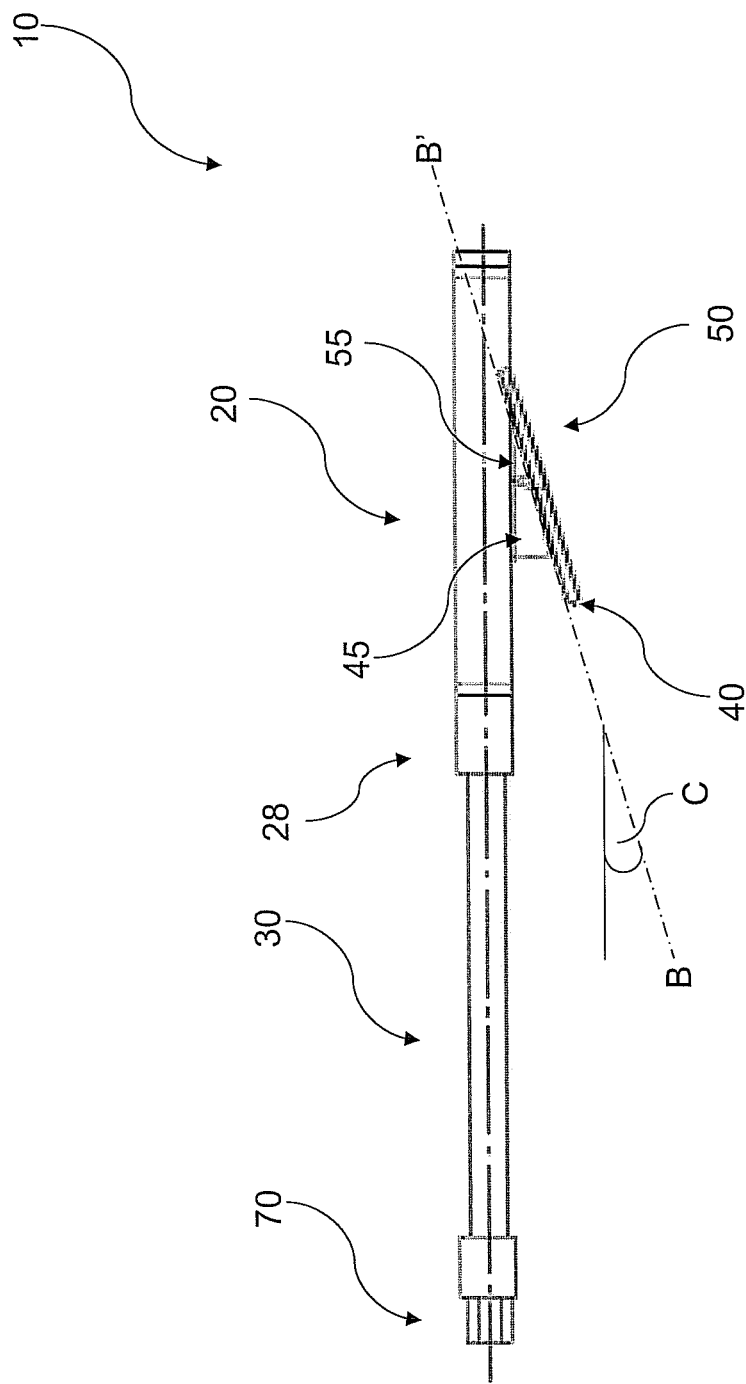
FIG. 5 is a top view of the distractor device of FIG. 1, the first and second mounting portions having first and second mounting surfaces, respectively, being shown in a same plane to each other and being offset with respect to a longitudinal axis of a body of the distractor device.
Figure 6:
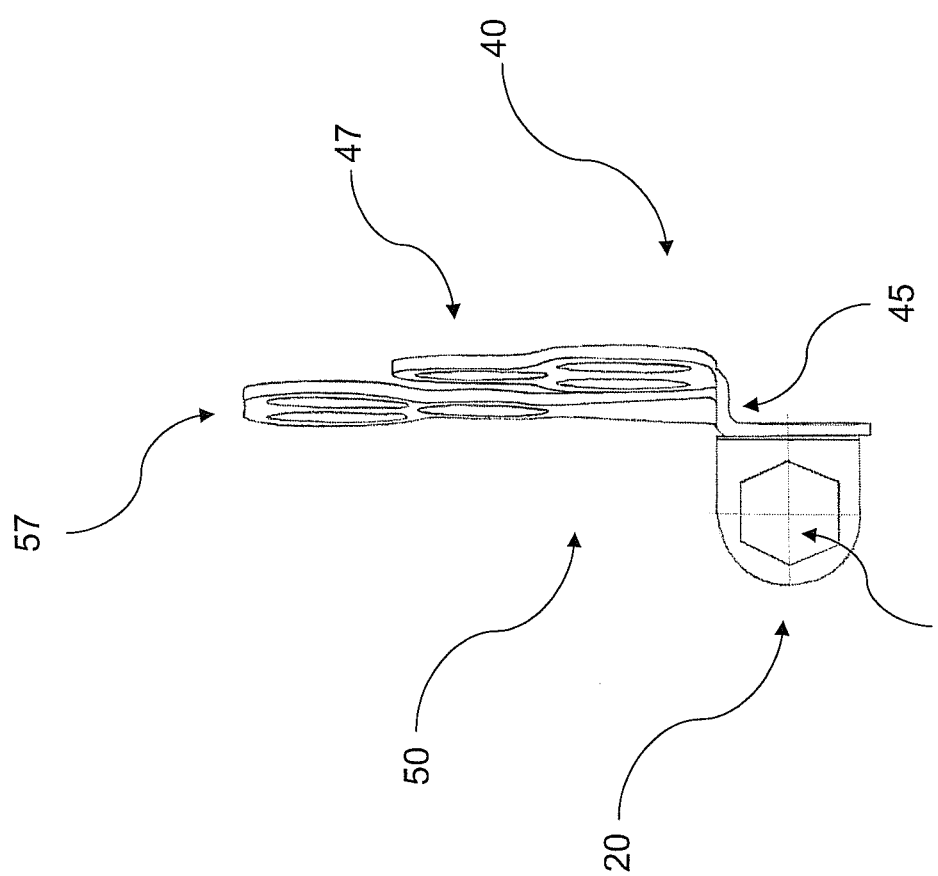
FIG. 6 is a front end view of the distractor device of FIG. 5.

As shown in FIGS. 5 and 6, the first and second mounting surfaces of the corresponding first 47 and second 57 mounting portions lie in substantially the same plane as each other. The plane of the first and second mounting surfaces, indicated by line B-B' in FIG. 5, is oriented at an angle "C" relative to the longitudinal axis of the body 20, where the longitudinal axis of the body 20 is aligned with a vector of distraction of the distractor device 10 in use. Offset angle "C" will be fixed relative to the longitudinal axis of the body 20. Therefore, the distraction device 10 having first and second mounting surfaces offset at an appropriate angle for the patient will be selected prior to the distraction procedure depending on whether flaring of the posterior segments is anticipated to be an issue for the particular patient during distraction. Reducing flaring of the posterior segments increases the chances of the upper and lower molars interdigitating. In addition, offset angle "C" also reduces the risk of a cross bite occurring between the respective second molars of the upper and lower jaw, and thus reduces the chances of a subsequent anterior open bite developing between the front or forward incisor teeth of each jaw as distraction proceeds. Offset angle "C" will generally fall within the range of between 0 degrees and 25 degrees, and for the majority of patients, within the narrower range of between 0 degrees and 15 degrees.

In other embodiments, it will be appreciated that the first and second mounting surfaces are not limited to lying substantially in the same plane, but may lie in different planes depending on, for example, the anatomy of the anterior and posterior segments, or the positions of the crowns or roots of the first and second molars.

As shown in FIGS. 1 to 4, the first 47 and second 57 mounting portions each comprise three lobes, with each lobe comprising one aperture, generally given reference numeral 60. The three apertures 60 in each mounting portion are arranged to define a triangle. Such a triangular arrangement of apertures ensures 60 that the first 47 and second 57 mounting portions are firmly mounted via their respective first and second mounting surfaces to the anterior and posterior segments, respectively.

The distractor device 10 further comprises six screws (not shown), in which each screw is adapted for locating in one of the three apertures 60 of the first 47 and second 57 mounting portions to mount the first mounting portion 47 via the first mounting surface to the anterior segment and the second mounting portion 57 via the second mounting surface to the posterior segment, respectively. The three apertures 60 in the first 47 and second 57 mounting portions are each sized to accommodate commercially available screws used for bone fixation. In this embodiment, the diameters of the apertures 60 are designed to accommodate 1.5 mm or 2.0 mm standard osseous fixation screws (not shown). Such screws comprise a head portion (not shown) and a shank portion (not shown), where the apertures 60 in the first 47 and second 57 mounting portions are also designed to accommodate the head portion of such screws. The size of screw to be used for each patient will be determined by the user fitting the distractor device 10. The triangular arrangement of apertures 60 ensures that when the screws are received in a corresponding one of the three apertures 60, the first 47 and second 57 mounting portions are firmly mounted via their respective first and second mounting surfaces to the anterior and posterior segments, respectively.

Figure 2:
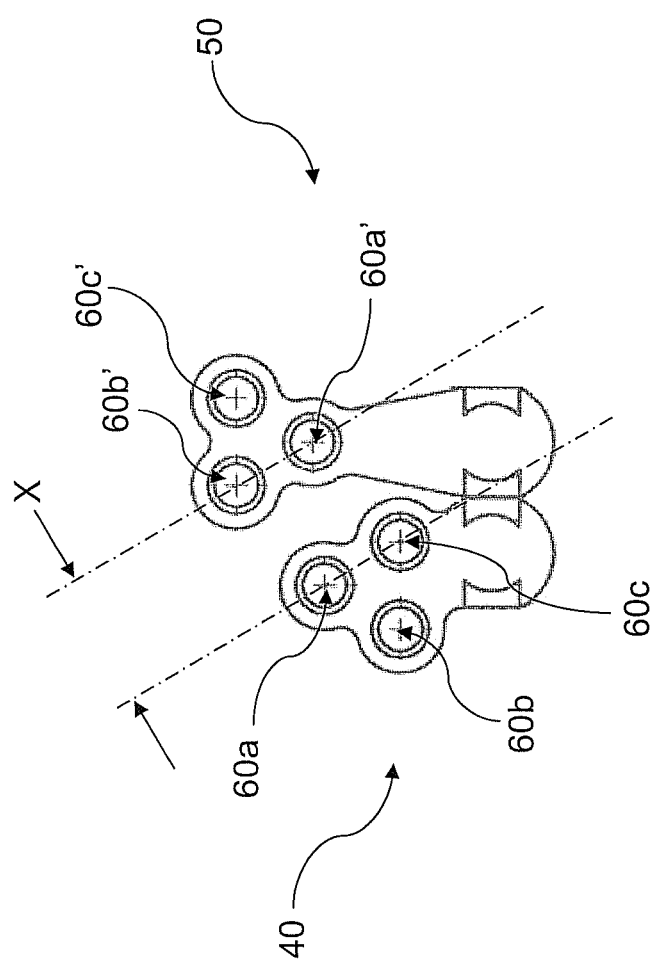
FIG. 2 is a schematic representation of the first and second mounting portions of FIG. 1, each comprising three apertures.

Referring specifically to FIG. 2, the first mounting portion 47 has a first aperture $60a$ of the three apertures being located further from the body 20 of the distractor device 10 than the other two apertures $60b$, $60c$, and the second mounting portion 57 has a first aperture $60a'$ of the three apertures being located closer to the body 20 than the other two apertures $60b'$, $60c'$. The triangular arrangement of apertures 60 for the first 47 and second 57 mounting portions being oppositely oriented to each other ensures that the distance between the first 47 and second 57 mounting portions is sufficient so as not to crowd the osteotomy when the distractor device 10 is mounted to the patient's jaw bone. By arranging the two sets of triangular arrangements of apertures 60 in this manner, the nearest apertures of the first 47 and second 57 mounting portions, which in this case are $60a$, $60c$ and $60a'$, $60b'$, respectively, are separated by a distance "X" that is sufficiently wide to allow screws (not shown) to be inserted into these nearest apertures 60 to secure the first 47 and second 57 mounting portions via their respective first and second mounting surfaces to the anterior and posterior segments, respectively, without first having to unnecessarily increase the distance between the first 40 and second 50 fixing members in order to do so, as is often the case with other distractor devices 10. This is therefore, beneficial as it maximises the actual distance available for the distraction to occur.

As shown in FIGS. 1 and 2, the first fixing member 40 is shorter in length than the second fixing member 50. In this arrangement, the triangular arrangement of apertures 60 for the first mounting portion 47 is distanced from the triangular arrangement of apertures 60 for the second mounting portion 57, such that the first 47 and second 57 mounting portions are substantially distanced from each other so as not to crowd the osteotomy when the distractor device 10 is mounted on the patient's jaw bone. However, it will be appreciated that in other embodiments, it may be necessary for the second fixing member 50 to be shorter in length than the first fixing member 40 (see, for example, FIGS. 3 (*v*) to (*viii*)).

In other embodiments, it will be appreciated that the triangular arrangements of apertures 60 in the first 47 and second 57 mounting portions, and the relative lengths of the first 40 and second 50 fixing members, may both be different to that described above to enable the separation distance "X" to be sufficiently wide to allow the screws to be inserted into the apertures 60 without being too close to the osteotomy.

Figure 3:
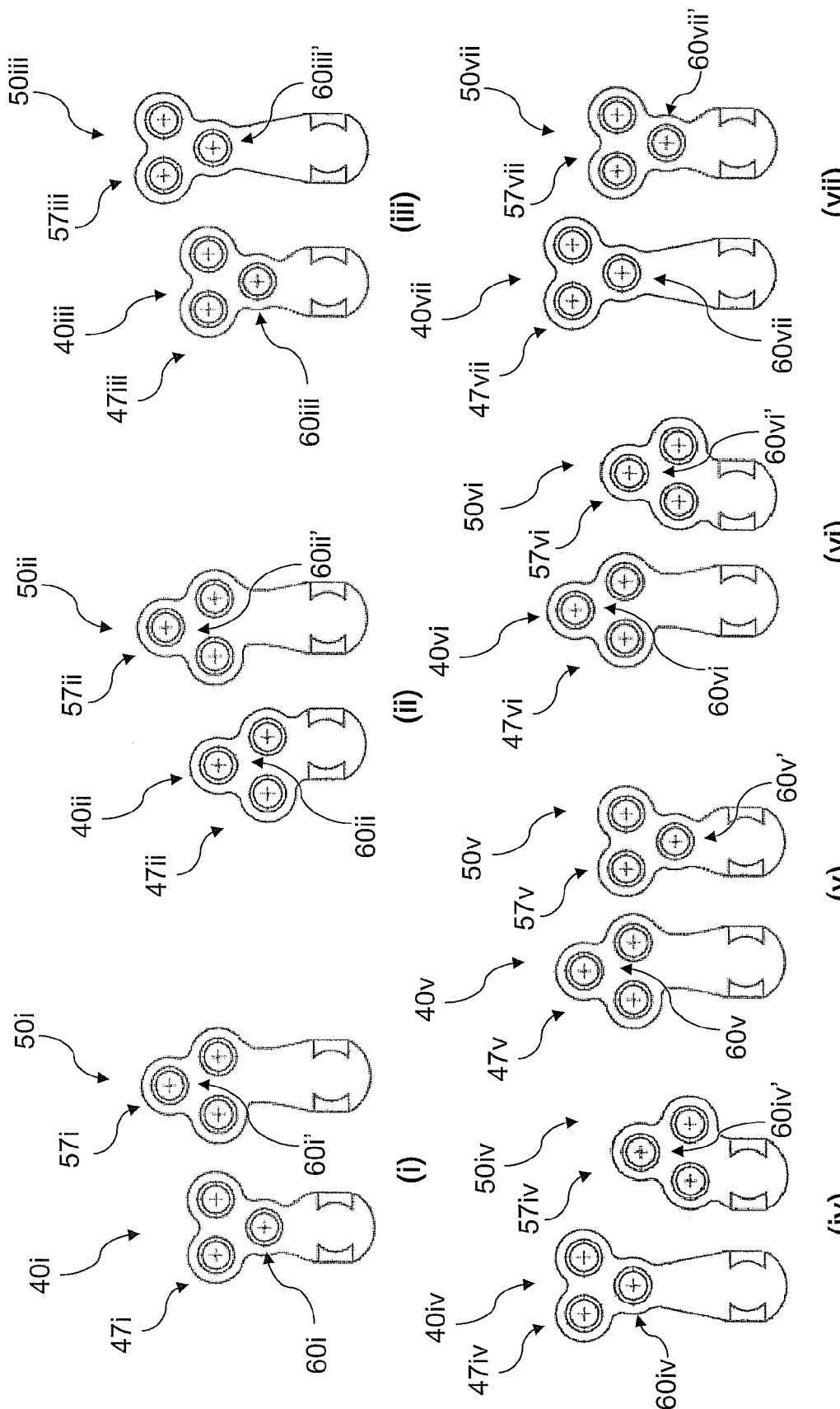
FIG. 3 is a schematic representation showing different pairing combinations of first and second fixing members.

For example, and referring specifically to FIG. 3, there is shown different pairing combinations of first (40*i* to 40*vii*) and second (50*i* to 50*vii*) fixing members, in which the relative lengths of the first (40*i* to 40*vii*) and second (50*i* to 50*vii*) fixing members, and the orientations of the respective sets of triangular arrangements of apertures of the corresponding first (47*i* to 47*vii*) and second (57*i* to 57*vii*) mounting portions, are varied to satisfy the above criterion. With respect to differing lengths, FIGS. 3 ((*i*) to (*iii*)) show different pairing combinations of the first (40*i* to 40*iii*) and second (50*i* to 50*iii*) fixing members, in which the length of the first fixing member (40*i* to 40*iii*) is shorter than the second fixing member (50*i* to 50*iii*). While FIGS. 3 (*iv*) to (*vii*) show different pairing combinations of the first (40*iv* to 40*vii*) and second (50*iv* to 50*vii*) fixing members, in which the length of the first (40*iv* to 40*vii*) fixing member is longer than the second (50*iv* to 50*vii*) fixing member.

With respect to the differing orientations of the triangular arrangement of apertures, FIGS. 3 (*ii*) and (*vi*) both show the triangular arrangements of the two respective sets of apertures of the first (47*ii*, 47*vi*) and second (57*ii*, 57*vi*) mounting portions as "pointing up" in the sense that the first aperture (60*ii*, 60*vi*) of the first (47*ii*, 47*vi*) mounting portion and the first aperture (60*ii'*, 60*vi'*) of the second (57*ii*, 57*vi*) mounting portion are located further from the body 20 than the other apertures in the triangle. While, FIGS. 3 (*iii*) and (*vii*) both show the triangular arrangements of the two respective sets of apertures of the first (47*iii*, 47*vii*) and second (57*iii*, 57*vii*) mounting portions as "pointing down" in the sense that the first aperture (60*iii*, 60*vii*) of the first (47*iii*, 47*vii*) mounting portion and the first aperture (60*iii'*, 60*vii'*) of the second (57*iii*, 57*vii*) mounting portion are located closer to the body 20 than the other apertures in the triangle.

Figs. (i) and (iv) show the triangular arrangement of apertures of the first (47*i*, 47*iv*) mounting portion as "pointing down" in the sense that the first aperture (60*i*, 60*iv*) is located closer to the body 20 than the other two apertures in the triangle, and the triangular arrangement of the apertures of the second (57*i*, 57*iv*) mounting portion as "pointing up" in the sense that the first aperture (60*i'*, 60*iv'*) is located further from the body 20 than the other two apertures in the triangle. While FIG. (v) shows the triangular arrangement of apertures of the first 47*v* mounting portion as "pointing up" in the sense that the first aperture 60*v* is located further from the body 20 than the other two apertures in the triangle, and the triangular arrangement of apertures of the second 57*v* mounting portion as "pointing down" in the sense that the first aperture 60*v'* is located closer to the body 20 than the other two apertures in the triangle.

In all of the above described pairing combinations of first (40*i* to 40*vii*) and second (50*i* to 50*vii*) fixing members in FIG. 3, it will be appreciated that by orienting the triangular arrangements of apertures in the first (47*i* to 47*vii*) and second (57*i* to 57*vii*) mounting portions relative to one another, or by adjusting the length of one of the first (40*i* to 40*vii*) and second (50*i* to 50*vii*) fixing members, the distance between the nearest apertures of the first (47*i* to 47*vii*) and second (57*i* to 47*vii*) mounting portions can be maximized to allow the screws to be inserted into the nearest apertures without crowding occurring between the nearest apertures of the two mounting portions and generally around the osteotomy itself. As such, the first 47 and second 57 mounting portions can be mounted via their respective first and second mounting surfaces to the anterior and posterior segments of the jaw bone, respectively, at locations much closer to the osteotomy than can normally be achieved with current distractor devices (not shown) prior to initiating the distraction, thereby ensuring that the maximum possible displacement of the first 47 and second 57 mounting portions and thus the lengthening of the jaw bone can be achieved through distraction.

Figure 4:
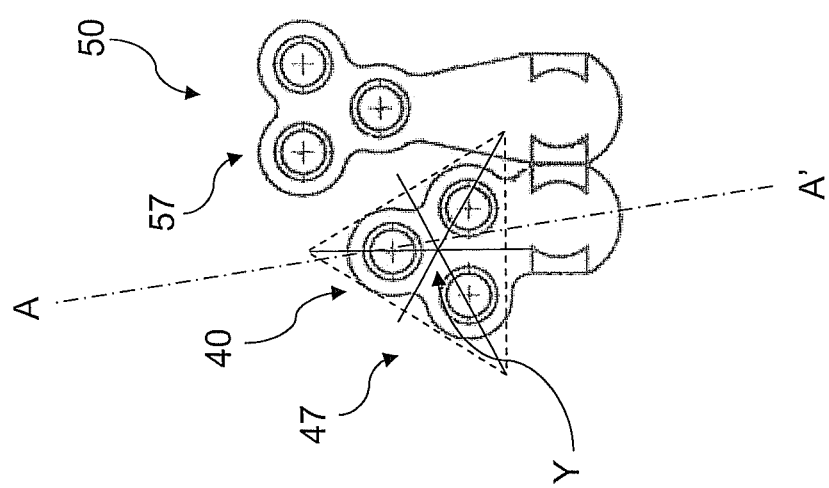
FIG. 4 is a schematic representation of the first and second fixing members of FIGS. 1 and 2, a centroid of the three apertures of the first mounting portion of the first fixing member being offset from a longitudinal axis of the first fixing member.

Referring specifically to FIG. 4, it is shown that a centroid "Y" of the triangle of the three apertures 60 of the first mounting portion 47 is positioned offset from the longitudinal axis of the first fixing member 40, as indicated by the dotted line along A-A'. By angling the first mounting portion 47 away from the second mounting portion 57 by offsetting the first mounting portion 47 from the longitudinal axis of the first fixing member 40 ensures that the first 47 and second 57 mounting portions are substantially distanced from each other so as not to crowd the osteotomy.

In other embodiments, it may be necessary for the centroid (not shown) of the triangle of the three apertures 60 of the second mounting portion 57 to be offset (not shown) from the longitudinal axis of the second fixing member 50. It will be appreciated that in this arrangement, the centroid of the three apertures 60 of the second mounting portion 57 is offset in a generally opposite direction to that shown for centroid "Y" in FIG. 4 such that the nearest apertures 60 of the first 47 and second 57 mounting portions are sufficiently separated from each other to enable a firm mounting to be established between the first and second mounting surfaces and the anterior and posterior segments, respectively, of the jaw bone so as not to crowd the osteotomy. It will also be appreciated that the angle at which the longitudinal axis of the first 40 and second 50 fixing members is oriented with respect to the longitudinal axis of the body 20 may vary depending on the relative sizes of the first 47 and second 57 mounting portions, and on the relative lengths of the first 40 and second 50 fixing members, and the overall need to maintain a greater separation distance as possible between the first 47 and second 57 mounting portions to reduce the risk of crowding the osteotomy, and ensuring that the screws can be inserted into the respective apertures 60 without being too close to the osteotomy.

In other embodiments, it will be appreciated that the number of apertures 60 in the first 47 and second 57 mounting portions is not limited to three, but may be more or less, depending on the intraoral application required for the distractor device 10. For example, where the distractor device 10 is for use on an adolescent, it may be necessary to use smaller first 47 and second 57 mounting portions, which may mean fewer apertures due to the size of the mounting portions relative to the size of the patient. Alternatively, where the distractor device 10 is to be used on, for example, an adult, it may be necessary to use larger first 47 and second 57 mounting portions, which may require more apertures to ensure a firm mounting between the first and second mounting surfaces and the anterior and posterior segments of the jaw bone, respectively.

In use, bilateral distraction of a patient's jaw bone in a controlled manner, particularly a retruded jaw bone, using a distraction device 10 attached to each of the left and right mandibles of the patient is achieved according to the following method.

Firstly, a crevicular incision is created in the gingiva of each of the left and right mandibles of the patient's jaw bone from the lateral incisor tooth to the second molar. The incisions are created such that they are aligned with the external oblique ridge of the corresponding left or right mandible of the jaw bone, and extend forwardly to include the papilla between the canine and lateral incisor tooth. A relief incision is then created vertically in the labial sulcus in each of the left and right mandibles. The muco-periosteal buccal flap or pocket created as a result of the incisions exposes the jaw bone from the vertical ramus to the lateral relief incision.

Secondly, a corticotomy cut is created in both the left and right mandibles by cutting the cortical bone laterally from the inter-dental buccal bone (i.e. between the space between the first and second molars) of each of the left and right mandibles to the bottom of the corresponding mandible. The cortical cut is made in the bone cortex only using a flat fissure oral surgical bur to give a width of generally ~1.5 mm.

Thirdly, a distraction device 10 is attached to each of the left and right mandibles of the jaw bone. The distraction device 10 shown in FIGS. 1, 5 and 6 is configured for attaching to the right mandible. It will be appreciated that the distractor device 10 to be attached to the left mandible is similar, albeit a mirror image of the distractor device 10 shown in FIGS. 1, 5 and 6.

Figure 7:
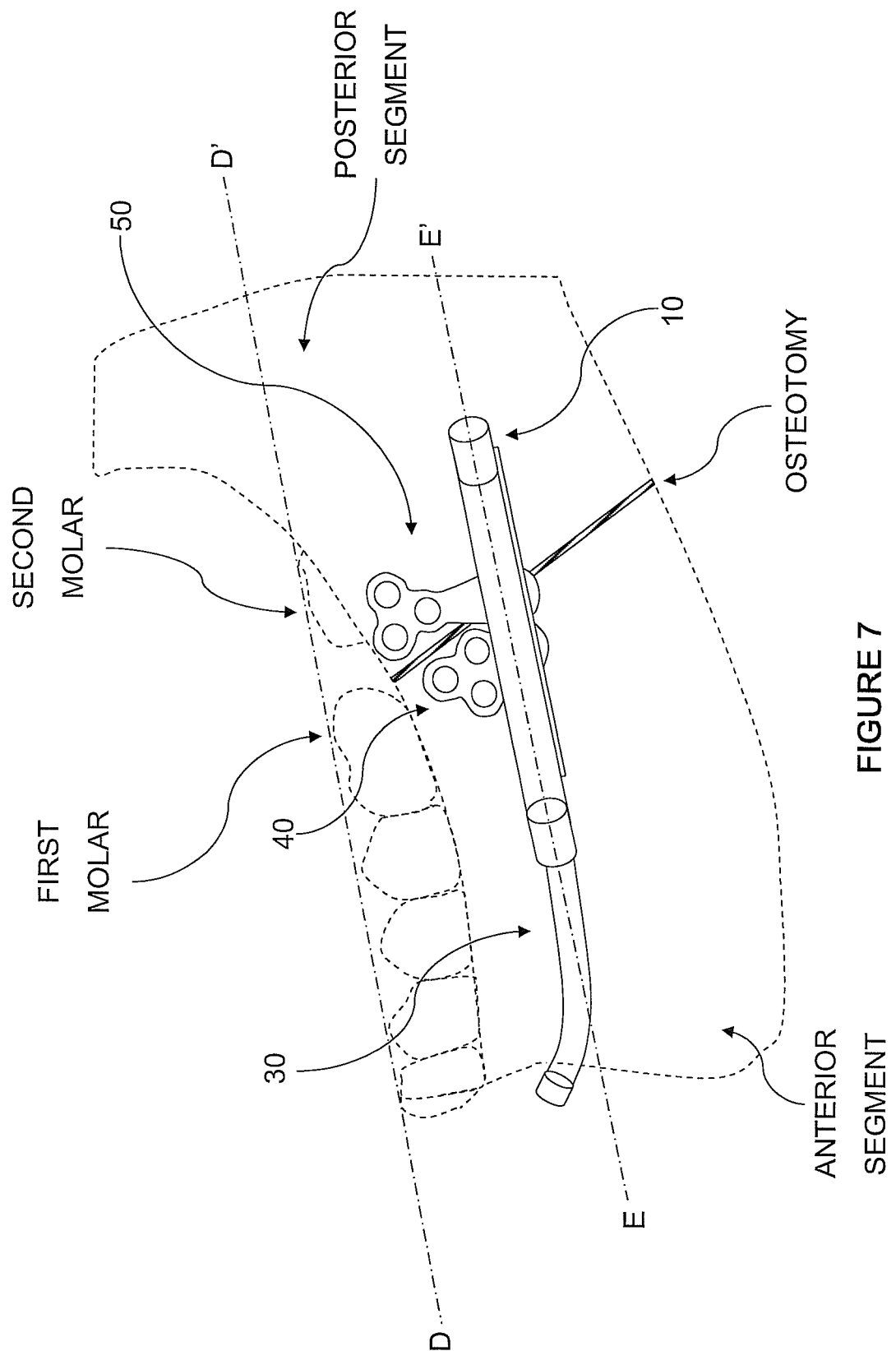
FIG. 7 is a schematic representation of the distractor device of FIG. 1 mounted to a jaw bone divided by an osteotomy into an anterior segment and posterior segment, the anterior segment being distracted from the posterior segment in an anterior direction along a distraction vector that is parallel to an occlusal plane of the lower jaw of the person.
Figure 8:
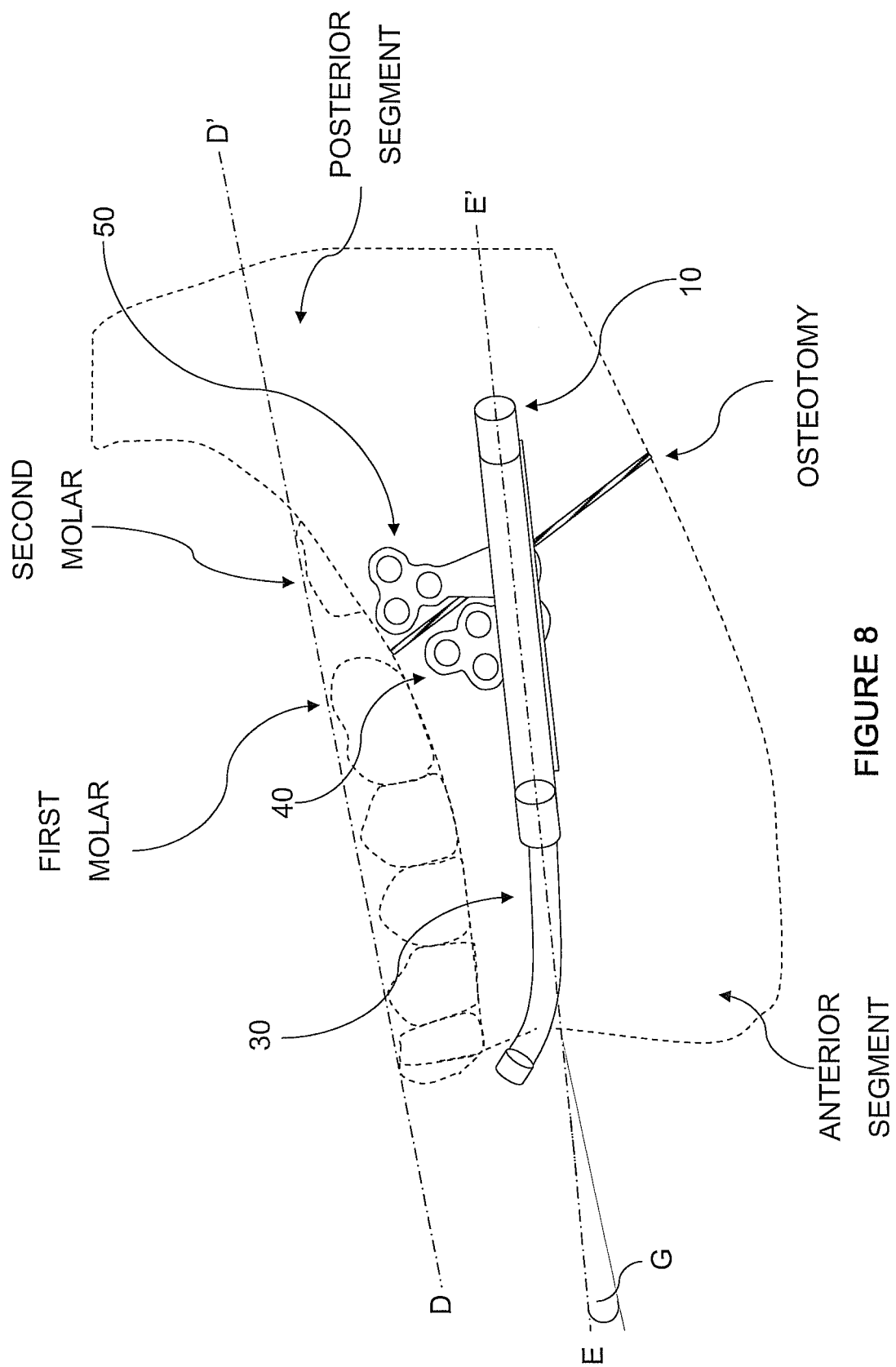
FIG. 8 is a schematic representation of the distractor device of FIG. 1 mounted to a jaw bone divided by an osteotomy into an anterior segment and posterior segment, the anterior segment being distracted from the posterior segment in an anterior direction along a distraction vector that slopes upwardly towards an occlusal plane of the lower jaw of the person.

The longer of the two fixing members of each distractor device 10, namely the second fixing member 50, is applied to the vertical ramus of the corresponding left or right mandible of the jaw bone such that the triangular arrangement of apertures 60 is oriented with the forward two apertures 60a' and 60b' being located approximately parallel with and just behind the buccal corticotomy cut (see FIGS. 2, 7 and 8). The shorter first fixing member 40 is then applied forward of the corticotomy cut such that the triangular arrangement of apertures is oriented with the rear two apertures 60a and 60c being located approximately parallel with and just in front of the buccal corticotomy cut, such that the first 47 and second 57 mounting portions are attached across the corticotomy cut, and subsequently, across the soon-to-be osteotomy cut. While the holes directly adjacent the corticotomy cut are positioned so that they run approximately parallel to the cut, it will be appreciated in a practical environment, the position of these drilled holes will largely depend on the anatomy of the patient being treated and the nature of the osteotomy being performed.

Prior to drilling holes in the left and right mandibles to receive screws to fix the first 47 and second 57 mounting portions via their respective first and second mounting surfaces to the corresponding mandible, the body 20 of the distractor device 10 is placed into the periosteal buccal pocket, and oriented laterally to the external oblique ridge of the vertical ramus of the corresponding mandible, such that the general lie of the activator 30 lies above the mental nerve exit from the mental nerve foramen. Holes are then drilled into the left and right mandibles using the triangular arrangement of apertures 60 as guides, and screws are then used to attach the first 47 and second 57 mounting portions of each distractor device 10 to the contours of the corresponding mandible.

Fourthly, once the holes for the apertures 60 have been drilled, the distractor devices 10 are removed, and inter-dental osteotomy cuts are then made to the left and right mandibles at the location of the corresponding corticotomy cuts. To achieve this, a fine osteotome is introduced into each corticotomy cut, and lightly hammered into the mandibular bony medulla, between the distal root of the lower first molar, and the mesial root/crown of the lower second molar. The osteotome is introduced into the lower cortex of the mandible, and lightly hammered in place. A Smiths surgical osteotomy distractor is then introduced into the corticotomy cut, and gradually opened to effectively create a crack propagation of the corresponding mandible, between the first and second molar teeth. As the crack progresses, eventually it comes to reach the lingual plate, where the crack may progress either spontaneously, or with assistance of both the Smiths distractor and the osteotome. Once the crack is fully extended from lateral (buccal) to lingual in each of the left and right mandibles, the respective anterior and posterior segments of the jaw bone are fully mobilised, such that both sides of the osteotomy are clearly separated from each other, and the anterior segment is free from the two posterior segments.

Fifthly, the first 47 and second 57 mounting portions of each distractor device 10 are then re-attached via their respective first and second mounting surfaces to the anterior and posterior segments, respectively, of the now separated jaw bone by inserting a screw through each of the apertures 60 and screwing it into the corresponding pre-drilled hole of the left or right mandible such that the first 47 and second 57 mounting portions of each of the distractor devices 10 are attached across the corresponding osteotomy. Each distractor device 10 is then essentially buried within the corresponding periosteal pocket on either side of the mouth by closing the wound through reapplying the muco-periosteal flap to its anatomical position, such that only the second end of the activator 30 with the turnkey 70 protrudes from the closed wound. The activators 30 of the two distractor devices 10 are oriented such that they extend forwardly into the lower labial sulcus and meet, approach, or cross over each other at the midline of the labial sulcus. The activators 30 are generally bent such that they are oriented slightly upwards behind the lower lip, and forward of the lower incisor teeth. The location of the previous vertical relief incisions made during original access, allows the second end of the activator 30, to protrude approximately 10-15 mm from each side to enable access to the corresponding turnkey 70.

Once the distractor devices 10 are mounted to the corresponding left and right mandibles of the jaw bone, the body 20 of each distractor device 10 is oriented such that rather being angled generally downwards as is the case when such conventional distractor devices are used, the body 20 of the distractor device 10 is either parallel to (see FIG. 7) or slopes upwardly towards (see FIG. 8), an occlusal plane of the lower jaw of the patient to which the distractor devices 10 are attached. The angle between the longitudinal axis of the body 20 of each distraction device 10 when mounted to the patient's jaw bone and the mean occlusal plane of the lower jaw defines the distraction vector of the distractor devices 10 along which the first mounting portion 47 moves relative to the second mounting portion 57. The effect of this upwardly directed distraction vector is to advance the anterior segment, and the anterior incisor teeth, forward and upward towards the occlusal plane of the lower jaw, with the intention of opening the middle of the occlusion, or bite. The angle subtended by the distraction vector and the occlusal plane of the lower jaw will generally fall within the range of between 0 degrees and 25 degrees, and for the majority of patients, within the narrower range of between 0 degrees and 15 degrees. By angling the body 20 of each of the distractor devices 10 to be either parallel to, or upwardly sloping towards, the occlusal plane of the lower jaw, provides a natural vector, which when distracted along, allows for the correction of an undersized or under-grown lower jaw, with the subsequent alignment of the teeth of the upper and lower jaws or occlusion.

Referring specifically to FIG. 7, the direction vector (indicated by line E-E') is shown oriented at 0 degrees relative to the occlusal plane of the lower jaw is (indicated by line D-D'), such that the vector of distraction is parallel to the occlusal plane of the lower jaw. In this arrangement, the anterior segment is distracted from the posterior segment in an anterior direction along the distraction vector that is parallel to the occlusal plane of the lower jaw.

Referring specifically to FIG. 8, the angle "G" subtended by the direction vector (indicated by line F-F') and the occlusal plane of the lower jaw (indicated by line D-D') lies within the range between 0 and 15 degrees. In this arrangement, the anterior segment is distracted from the posterior segment in an anterior direction along the distraction vector that slopes upwardly by angle "G" towards the occlusal plane of the lower jaw.

With distractor devices 10 applied to the left and right mandibles of the jaw bone, the two distractor devices 10 make an inter-distractor angle to each other, which is dependent on offset angle "C" (see FIG. 5) defined by the plane (indicated by line B-B') between the first and second mounting faces of the first 47 and second 57 mounting portions, respectively, and the longitudinal axis of the body 20 of the distractor device 10. It will be appreciated that the offset angle "C" for each distractor device 10 is fixed relative to the longitudinal axis of the body 20. Therefore, the distraction device 10 having first and second mounting surfaces offset at an appropriate angle for the patient will be selected prior to the distraction procedure depending on whether flaring of the posterior segments is anticipated to be an issue for the particular patient during distraction. The inter-distractor angle between the two distractor devices 10 is such that as distraction proceeds, the vertical ramus of each of the left and right mandibles flares laterally, improving the posterior width of the lower face of the patient.

As bilateral distraction proceeds through incremental rotation of the activators 30 of the two respective distractor devices 10 at a particular distraction rate, the first fixing member 40 of each distractor device 10 moves linearly with respect to the second fixing member 50 with each rotation of the activator 30, on account of the end portion 45 of the first fixing member 40 being mounted to the activator 30 within the longitudinal groove 25 of the body 20 and the end portion 55 of the second fixing member 50 being fixed to the body 20. As such, the distance between the first 47 and second 57 mounting portions of each distractor device 10 increases with each rotation of the activator 30 relative to the body 20. Therefore, as the first mounting portion 47 is mounted via the first mounting surface to the anterior segment of the distracted jaw bone and the second mounting portion 57 is mounted via the second mounting surface to the posterior segment, manual rotation of the turnkey 70 of each activator 30 enables the anterior segment to be distracted forwardly of the posterior segment at an acceptable distraction rate until the desired distraction distance has been achieved.

The distraction rate will depend on the speed with which bone regeneration via the patient's own self-repair mechanism, can occur to fill the gap created between the anterior and posterior segments of the jaw bone as distraction proceeds. In certain cases, the ideal distraction rate may fall within the range of between 0.2 mm and 2.0 mm per day. However, in most cases, it will be expected that the distraction rate will fall within the narrower range of between 0.5 mm and 1.2 mm per day, achievable by rotating the turnkey 70 of the activator 30 through small increments throughout the day.

The distracting step of the method is repeated until the desired amount of distraction of the anterior segment from the posterior segments is achieved. Distraction is deemed to have been completed when it is determined that:
  (i) The lower incisors are in a normal relationship to the upper incisors, or
  (ii) The lower canines and premolars or first molar teeth are in normal relationship to the upper teeth.

The distractor devices 10 are then removed, using a buccal sulcus incision, traced along the body 20 of the corresponding distractor device 10, and removal of the distractor device 10 is via the mouth.

A combination of the reversed orientations of the triangular arrangements of apertures 60 of the first 47 and second 57 mounting portions, the shorter length of one of the first and second fixing members relative to the other member, the orientation of the apertures 60 relative to the osteotomy cut, and the orientation of the first and second mounting surfaces relative to the longitudinal axis of the body 20 of the distractor device 10, enables a number of key advantages:
  (i) The means to correct the effects of having a developmentally smaller lower jaw (relative to the upper jaw), including:
    a. Opening of the posterior tongue airway, which is naturally constricted in the conditions which feature a relatively smaller lower jaw;
    b. Expanding the circumference of the mandible, to enable for the normal intra-arch alignment of otherwise crowded lower teeth;
    c. Creation of an inter-molar space to enable for orthodontically-controlled intra-arch alignment of teeth;
    d. Correcting the relationship of the lower arch of teeth relative to the upper arch of teeth, such that they may develop a normal inter-arch dental relationship (that is, develop a normal occlusion);
    e. By correcting at an early enough age, to offset the development of compensatory and abnormal secondary growths of particularly the upper jaw, or maleruptions of teeth, which arise because of a developmentally relatively smaller lower jaw;
    f. For correcting the normal facial proportions, and the relative relations between the upper and lower jaws in terms of their inter-mutual development.
  (ii) The mounting portion of the longer fixing member being mounted to the external oblique ridge of the corresponding mandible enables holes in the left and right mandibles to be drilled entirely via access through the patient's mouth as opposed to having to make an incision in the patient's cheek using a surgical trocar and drilling the holes via the cheek.
  (iii) The osteotomy cut can be made to the left or right mandible entirely via access through the patient's mouth as opposed to having to make an incision in the patient's cheek using a surgical trocar and making the osteotomy cut via the cheek.

(iv) The distractor device 10 can be attached to the left or right mandible, and the distractor device 10 enclosed by flesh or mucosa, such that only the second end of the activator 30 is accessible, thereby making the distractor device 10 imperceptible.

(v) The reversed orientation of the triangular arrangement of apertures 60 of the first 47 and second 57 mounting portions enabling the mounting portions to be located much closer to the osteotomy cut such that the first 40 and second 50 fixing members can be positioned relatively close together thereby maximising the possible distraction distance.

(vi) The screws for the first mounting portion 47 necessarily avoid the crown and roots of the first molar.

(vii) The orientation of the apertures 60 within each of the first 47 and second 57 mounting portions, and which lie beside the osteotomy cut, naturally align the corresponding mounting portions to this osteotomy cut, without causing the screws to impose upon the osteotomy cut, whilst the first 40 and second 50 fixing members are maximally closed towards each other, and which by way of their attachment to the activator 30 and body 20, respectively, provides for a natural orientation of the body 20 of the distractor device 10 in such a way, that following distraction, the occlusion is normalized, and the normal proportions and shape of the originally under-grown lower jaw, is maximally naturalized and corrected in terms of proportions and relations to the upper jaw.

(viii) The definition of a natural vector, which when distracted along, simultaneously between two complementary distractor devices 10, one on each of the left and right mandibles, allows for the correction of an undersized or under-grown lower jaw, with the subsequent alignment of the teeth of the upper and lower jaws or occlusion, whilst minimizing the actual size, length and bulk of the actual distractor devices 10, matched to the maximal advantage afforded by the length of the body 20 of the distractor devices 10.

Interpretation

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Definitions

The term "occlusal plane" is defined as a plane passing through the occlusal or biting surfaces of the teeth. It represents the mean of the curvature of the occlusal surface.

The term "vector of distraction" is defined as the line along which the first mounting portion moves relative to the second mounting portion.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the dental and medical industries.

The claims defining the invention are as follows:

1. A distractor device for distraction of a mandible divided at an osteotomy site between first and second molar teeth into an anterior segment and a posterior segment, the distractor device comprising:
   an elongate body having a longitudinal groove extending at least partly along the length of the body;
   a first fixing member having a first longitudinal axis, the first fixing member comprising:
      an end portion that is located within the longitudinal groove for travel therealong, and
      a mounting portion distal to the end portion having a mounting surface adapted for mounting to the anterior segment of the osteotomy site;
   a second fixing member having a second longitudinal axis offset from the first longitudinal axis, the second fixing member comprising:
      an end portion that is fixed within the longitudinal groove of the elongate body substantially adjacent the end portion of the first fixing member before distraction, and
      a mounting portion located distal to the end portion having a mounting surface adapted for mounting to the posterior segment of the osteotomy site;
   an activator member engaging with the elongate body, wherein at least the end portion of the first fixing member is adjustable along the longitudinal groove of the elongate body in an anterior direction by movement of the activator member relative to the body to distract the anterior segment in use;
   wherein the first fixing member and the second fixing member are spaced from the elongate body at different average lengths; and
   wherein positioning of the mounting portion of the first and second fixing members is effective so as not to crowd the osteotomy site, and allow improved displacement of the first fixing member relative to the second fixing member for incremental lengthening of the mandible through distraction of the anterior segment by the activation member.

2. A distractor device for distraction of a mandible divided at an osteotomy site into an anterior segment and a posterior segment according to claim 1, wherein the first mounting surface and the second mounting surface reside substantially in the same plane, and oriented at an angle of between 0.1 degrees and 30 degrees to the vector of distraction.

3. A distractor device for distraction of a mandible divided at an osteotomy site into an anterior segment and a posterior segment according to claim 1, wherein the longitudinal axis of the second fixing member is substantially perpendicular to the longitudinal axis of the elongate body.

4. A distractor device as claimed in claim 1, wherein the mounting portions of the first and second fixing members respectively comprise three lobes with each lobe comprising one aperture, wherein the three apertures in each mounting portion comprise a triangular arrangement of openings, and wherein the mounting portions of the first and second fixing members are substantially firmly mounted to the anterior and posterior segments respectively via their respective mounting surfaces.

5. A distractor device as claimed in claim 4, wherein the mounting portion of the first fixing member has a first aperture of the three apertures being located further from the elongate body than the other two apertures, and the mounting portion of the second fixing member has a first aperture of the three apertures being located closer to the elongate body than the other two apertures, wherein the triangular arrangement of openings for the first and second mounting portions being oppositely oriented so that the distance between the mounting portions of the first and second fixing members is sufficient so as not to crowd the osteotomy site when the distractor is mounted to anterior and posterior segments of a patient's mandible about the osteotomy site prior to distraction.

6. A distractor device as claimed in claim 4, wherein a centroid of the triangular arrangement of openings in the mounting portion of the first fixing member is offset from the longitudinal axis of the first fixing member.

7. A distractor device as claimed in any one of claims 4, wherein a centroid of the triangular arrangement of openings in the mounting portion of the second fixing member is offset from the longitudinal axis of the second fixing member, and wherein the centroid of the mounting portion of the second fixing member is offset in a generally opposite direction to that of the mounting portion of the first fixing member.

8. A distractor device as claimed in claim 4, further comprising at least six fasteners, each fastener being adapted for locating in one of the at least three apertures of the mounting portions of the first and second fixing members to mount the mounting portion of the first fixing member to the anterior segments of the osteotomy site and the mounting portion of the second fixing member to the posterior segment.

9. A distractor device as claimed in claim 1, wherein the first fixing member is shorter in average length than the second fixing member.

10. A distractor device as claimed in claim 1, wherein the activator member comprises an externally threaded portion and the elongate body comprises a complementary internally threaded portion to threadingly engage the externally threaded portion, the distance between the first and second fixing members being adjustable by rotation of the expansion member relative to the body in use.

11. A distractor device as claimed in claim 10, wherein the first fixing member is adapted to move linearly along the longitudinal groove with respect to the second fixing member.

12. A method of distracting a mandible of a person divided by osteotomy into an anterior segment and at least one posterior segment using at least one distractor device according to claim 1, the method comprising the steps of:
    attaching a mounting portion of the first fixing member to the anterior segment;
    attaching a mounting portion of the second fixing member to the posterior segment such that the mounting portions of the first and second fixing members are attached across the osteotomy site; and
    distracting the anterior segment from the posterior segment in an anterior direction along a distraction vector that slopes upwardly towards an occlusal plane of the lower jaw of the person.

13. A method as claimed in claim 12, wherein the angle subtended by the distraction vector and the occlusal plane of the lower jaw is between 0.1 and 25 degrees.

14. A method as claimed in claim 12, wherein the angle subtended by the distraction vector and the occlusal plane of the lower jaw is between 0.2 and 20 degrees.

15. A method as claimed in claim 12, wherein the at least one distractor device is two distractor devices, the first and second mounting portions of a first of the two distractor devices being attached to a left mandible and the first and second mounting portions of a second of the two distractor devices being attached to a right mandible.

16. A method as claimed in claim 15, wherein the at least one posterior segment is two posterior segments, the first mounting portion of each of the two distractor devices being attached to the anterior segment and the second mounting portion of each of the two distractor devices being attached across the osteotomy to a corresponding posterior segment of the two posterior segments.

17. A method as claimed in claim 12, wherein the anterior segment is distracted from the at least one posterior segment by between 0.2 mm and 20 mm each day.

18. A method as claimed in claim 12, wherein the anterior segment is distracted from the at least one posterior segment by between 0.5 mm and 15 mm each day.

19. A method as claimed in claim 12, wherein the anterior segment is distracted from the at least one posterior segment by between 0.7 mm and 12 mm each day.

20. A method as claimed in claim 12, further comprising the step of:
repeating the distracting step until the desired amount of distraction is achieved.

21. A method of distracting a jaw bone of a person divided by osteotomy into an anterior segment and at least one posterior segment using at least one distractor device according to claim 1, the method comprising the steps of:
attaching a mounting portion of the first fixing member to one of the anterior segment and the at least one posterior segment;
attaching a second mounting portion of the second fixing member to the other segment of the anterior segment and the at least one posterior segment, such that the mounting portions of the respective fixing members are attached across the osteotomy site; and
distracting the anterior segment from the at least one posterior segment in an anterior direction along a distraction vector that is substantially parallel to an occlusal plane of the lower jaw of the person.

22. A method as claimed in claim 21, wherein the at least one distractor device is two distractor devices, the first and second mounting portions of a first of the two distractor devices being attached to a left mandible and the first and second mounting portions of a second of the two distractor devices being attached to a right mandible.

23. A method as claimed in claim 22, wherein the at least one posterior segment is two posterior segments, the first mounting portion of each of the two distractor devices being attached to the anterior segment and the second mounting portion of each of the two distractor devices being attached across the osteotomy to a corresponding posterior segment of the two posterior segments.

24. A method as claimed in claim 21, wherein the anterior segment is distracted from the at least one posterior segment by between 0.2 mm and 20 mm each day.

25. A method as claimed in claim 21, wherein the anterior segment is distracted from the at least one posterior segment by between 0.5 mm and 15 mm each day.

26. A method as claimed in claim 21, wherein the anterior segment is distracted from the at least one posterior segment by between 0.7 mm and 12 mm each day.

27. A method as claimed in claim 21, further comprising the step of:
repeating the distracting step until the desired amount of distraction is achieved.

28. A distractor device for distracting a jaw bone divided by osteotomy into an anterior segment and a posterior segment, the distractor device comprising:
an elongate body having a longitudinal groove extending at least partly along the length of the body;
an expansion member adapted to extend relative to the body along a vector of distraction;
a first fixing member extending from the expansion member and having a first mounting portion having a first mounting surface, the first mounting surface being adapted for mounting to one of the anterior and posterior segments; and
a second fixing member extending from the body and having a second mounting portion having a second mounting surface, the second mounting surface being adapted for mounting to the other of the anterior and posterior segments, the first mounting surface and the second mounting surface being in a substantially same plane and oriented at an angle of between 0.1 degrees and 30 degrees to the vector of distraction,
wherein the first mounting portion is positioned offset from the longitudinal axis of the first fixing member, and wherein the first mounting portion is angled away from the second mounting portion to distance the first and second mounting surfaces; and
wherein a distance between the first and second mounting portions being adjustable by movement of the expansion member relative to the body to distract the jaw bone in use.

29. A distractor device as claimed in claim 28, wherein the first mounting surface is mounted to the anterior segment and the second mounting surface is mounted to the posterior segment.

30. A distractor device as claimed in claim 28, wherein the angle is between 1 degree and 15 degrees.

31. A distractor device as claimed in claim 28, wherein the vector of distraction is aligned with the longitudinal axis of the body.

32. A distractor device as claimed in claim 28, wherein one of the first and second fixing members is shorter in length than the other fixing member.

33. A distractor device as claimed in claim 28, wherein the first fixing member is shorter in length than the second fixing member.

34. A distractor device as claimed in claim 28, wherein the second fixing member is shorter in length than the first fixing member.

35. A distractor device as claimed in claim 28, wherein the first and second mounting portions each comprise at least three apertures arranged to define a triangle.

36. A distractor device as claimed in claim 35, wherein the first mounting portion has a first aperture of the at least three apertures being located further from the body than the other apertures, and the second mounting portion has a first aperture of the at least three apertures being located closer to the body than the other apertures.

37. A distractor device as claimed in claim 35, wherein the first mounting portion has a first aperture of the at least three apertures being located closer to the body than the other apertures, and the second mounting portion has a first aperture of the at least three apertures being located further from the body than the other apertures.

38. A distractor device as claimed in claim 35, wherein the first and second mounting portions each have a first aperture of the at least three apertures being located further from the body than the other apertures.

39. A distractor device as claimed in claim 35, wherein the first and second mounting portions each have a first aperture of the at least three apertures being located closer to the body than the other apertures.

40. A distractor device as claimed in claim 35, further comprising at least six fasteners, each fastener being adapted for locating in one of the at least three apertures of the first and second mounting portions to mount the first mounting surface to one of the anterior and posterior segments and the second mounting surface to the other of the anterior and posterior segments, respectively.

41. A distractor device as claimed in claim 28, wherein the expansion member comprises an externally threaded portion and the body comprises a complementary internally threaded portion to threadingly engage the externally threaded portion, the distance between the first and second mounting portions being adjustable by rotation of the expansion member relative to the body in use.

42. A distractor device as claimed in claim 28, wherein the first fixing member is adapted to move linearly with respect to the second fixing member.

43. A distractor device as claimed in claim 28, wherein each of the first and second fixing members is elongate and has a longitudinal axis.

44. A distractor device as claimed in claim 43, wherein a centroid of the triangle of the at least three apertures of the first mounting portion is offset from the longitudinal axis of the first fixing member.

45. A distractor device as claimed in claim 43, wherein a centroid of the triangle of the at least three apertures of the second mounting portion is offset from the longitudinal axis of the second fixing member.

* * * * *